United States Patent [19]

Sakaguchi et al.

[11] Patent Number: 4,909,957
[45] Date of Patent: Mar. 20, 1990

[54] LIQUID CRYSTALLINE COMPOUNDS AND PROCESS FOR PRODUCTION THEREOF

[75] Inventors: Kazuhiko Sakaguchi, Toyonaka; Naoya Kasai, Amagasaki; Yoshikazu Takehira, Itami; Tohru Kitamura, Kyoto; Yutaka Shiomi, Amagasaki, all of Japan

[73] Assignee: Daiso Co., Ltd., Osaka, Japan

[21] Appl. No.: 241,209

[22] Filed: Sep. 7, 1988

[30] Foreign Application Priority Data

Sep. 7, 1987 [JP] Japan .................. 62-224756
Aug. 5, 1988 [JP] Japan .................. 63-196646

[51] Int. Cl.$^4$ ............... C09K 19/34; C07D 307/12; C07D 239/34; C07D 239/26
[52] U.S. Cl. ............... 252/299.61; 252/299.01; 544/298; 544/335; 549/322; 549/323; 549/508; 549/560
[58] Field of Search ............ 252/299.01, 299.61; 544/298, 335; 549/322, 323; 350/350 S

[56] References Cited

U.S. PATENT DOCUMENTS 4,818,431  4/1989  Eidenschink et al. ......... 252/299.61

FOREIGN PATENT DOCUMENTS 288813  11/1988  European Pat. Off. .
313379   4/1989  European Pat. Off. .
3739588  7/1988  Fed. Rep. of Germany .
56-128776 10/1981  Japan .
57-88174  6/1982  Japan .

Primary Examiner—John F. Terapane
Assistant Examiner—J. E. Thomas
Attorney, Agent, or Firm—Wegner & Bretschneider

[57] ABSTRACT

Liquid crystalline compounds having an optically active γ-lactone ring of the formula:

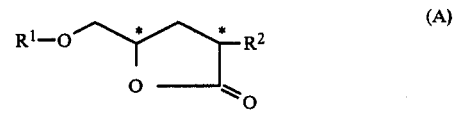

(A)

wherein $R^1$ is a group selected from the group consisting of

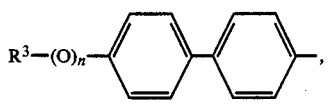

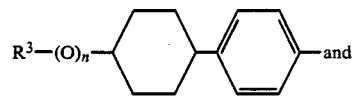
and

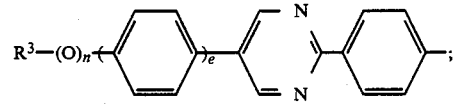

n and e are each independently 0 or 1; $R^3$ is an alkyl group having 1 to 15 carbon atoms; $R^2$ is a group of the formula: —(CO)$_m$—R$^4$; m is 0 or 1; $R^4$ is hydrogen atom or an alkyl having 1 to 15 carbon atoms; and the symbol * is an asymmetric carbon atom, and an intermediate thereof, and process for the production of the same.

5 Claims, 2 Drawing Sheets

LIQUID CRYSTALLINE COMPOUNDS AND PROCESS FOR PRODUCTION THEREOF

This invention relates to liquid crystalline compounds, intermediate compounds, and a process for the production thereof. More particularly, it relates to novel liquid crystalline compounds having optically active γ-lactone ring which are useful as an element for display devices or an element for opto-electronics devices. The liquid crystalline compounds of this invention include not only the compounds which can exhibit the liquid crystal phase by themselves but also the compounds which do not exhibit the liquid crystal phase alone but are useful as a component of liquid crystal compositions.

PRIOR ART

Liquid crystals have widely been used as a material for display devices, where TN (Twisted Nematic) type display system is usually employed. This TN display system has such advantages that it has less electric consumption, it gives less eye fatigue because it is a receptor type, and the like, but on the other hand, this system is disadvantageous in that the driving force is very weak because it is driven mainly on the basis of anisotropy of dielectric constant and it is slow in response speed, and hence, this system can not be applied to the devices which require high response speed.

Liquid crystal having ferroelectricity has first been found by R. B. Meyer et al. in 1975 (cf. J. Physique, 36, L-69, 1975). This liquid crystal is driven by a comparatively large force derived from spontaneous polarization and shows extremely high response speed and has also good memory. Owing to such excellent properties, the ferroelectric liquid crystal has been noticed as a new type of display element. In order to exhibit the ferroelectricity, the liquid crystalline compounds should show chiral smectic C phase (SmC* phase) and thus should contain at least one asymmetric carbon atom in the molecule. It is also necessary to have a dipole moment in the direction vertical to the long axis of the molecule.

A ferroelectric liquid crystal DOBAMBC synthesized by Meyer et al. has the following formula:

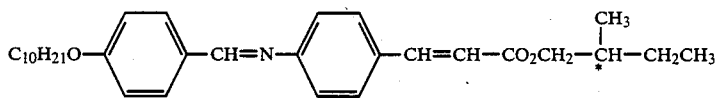

and satisfies the above conditions, but it contains a Schiff base and hence is chemically unstable and shows such a low spontaneous polarization as $3 \times 10^{-9}$ C/cm². Since then, there have been synthesized many ferroelectric liquid crystalline compounds, but any practically useful compound having sufficiently high response speed has never been found.

Among the known ferroelectric liquid crystalline compounds, DOBA-1-MBC which has the asymmetric carbon atom at the position nearer to the carbonyl group than in DOBAMBC and has the following formula:

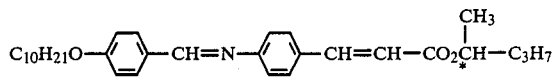

shows a spontaneous polarization of $5 \times 10^{-8}$ C/cm² which is larger than that of DOBAMBC. It is assumed that this will be caused by the following difference. That is, the asymmetric carbon atoms and the dipole which are important factors for the appearance of ferroelectricity are positioned close each other, and thereby, the free rotation of the dipole moiety of molecule is depressed and then the orientation of the dipole is increased. Thus, it is assumed that the known ferroelectric liquid crystalline compounds can not give satisfactory spontaneous polarization and high response speed because the asymmetic carbon atom having an inhibitory action of the free rotation of molecule is present on the linear chain in he known ferroelectric liquid crystalline compounds and hence the free rotation of molecule can not completely be inhibited and the dipole moiety can not be fixed.

SUMMARY DESCRIPTION OF THE INVENTION

Under the circumstances, the present inventors have intensively studied as to inhibition of free rotation of dipole moiety in the conventional ferroelectric liquid crystalline compounds and have found that the free rotation can be inhibited by providing a compound wherein the asymmetric carbon atom is contained in a 5-membered lactone ring, by which there can be obtained a chemically stable liquid crystalline compound having ferroelectricity.

An object of the invention is to provide novel ferroelectric liquid crystalline compound which is chemically stable and is useful as an element for display devices or an element for opto-electronics devices. Another object of the invention is to provide liquid crystalline compounds having optically active q-lactone ring in the molecule wherein one or two asymmetric carbon atoms are present in the 5-membered lactone ring. A further object of the invention is to provide a process for preparing the novel liquid crystalline compounds. These and other objects and advantages of the invention will be apparent to those skilled in the art from the following description.

DETAILED DESCRIPTION OF THE INVENTION

Figure 1:
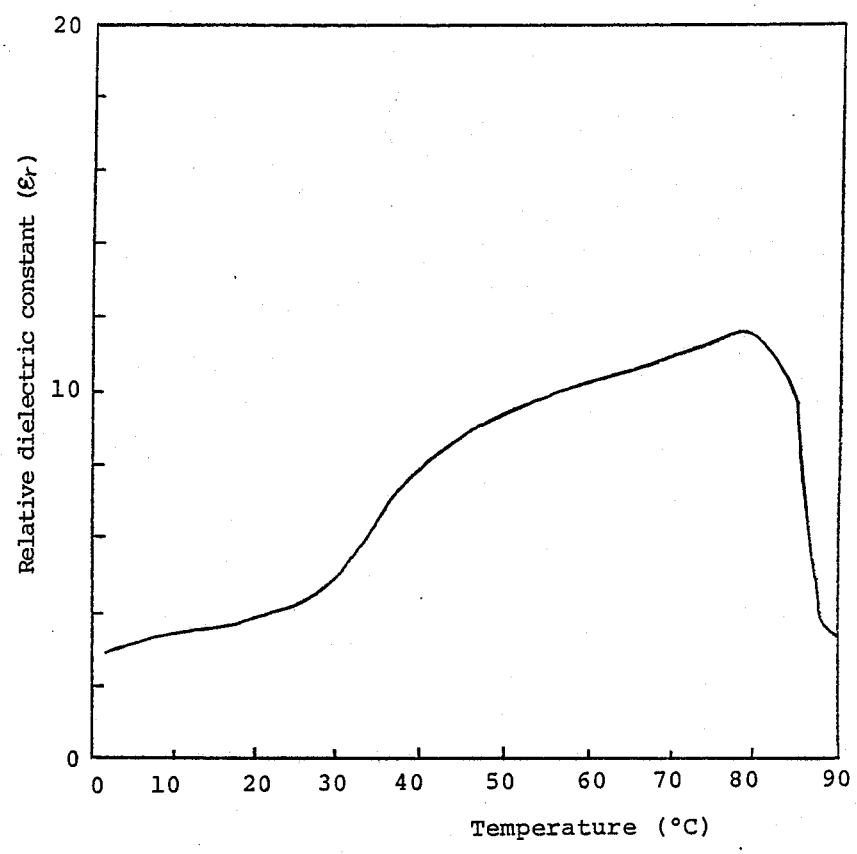
FIG. 1 shows a graph of the relation between the relative dielectric constant and temperature in the q-lactone derivative prepared in Example 1.

The novel liquid crystalline compounds of the invention are a compound having optically active q-lactone ring and having the following formula:

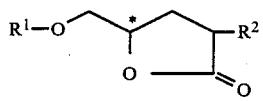 (A)

wherein $R^1$ is a group selected from the group consisting of

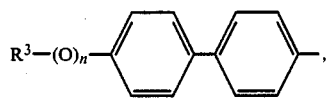,

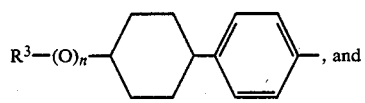, and

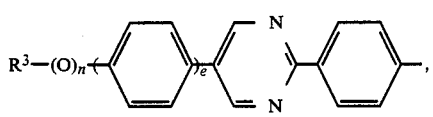, n and e are each independently 0 or 1, $R^3$ is an alkyl group having 1 to 15 carbon atoms, $R^2$ is a group of —$(CO)_m$—$R^4$, m is 0 or 1, and $R^4$ is hydrogen atom or an alkyl group having 1 to 15 carbon atoms, and * means an asymmetric carbon atom.

In the specification, the term "alkyl group" for $R^3$ and $R^4$ includes methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, isopropyl, t-butyl, 2-methylpropyl, 1-methylpropyl, 3-methylbutyl, 2-methylbutyl, 1-methylbutyl, 4-methylpentyl, 3-methylpentyl, 2-methylpentyl, 1-methylpentyl, 5-methylhexyl, 4-methylhexyl, 3-methylhexyl, 2-methylhexyl, 1-methylhexyl, 6-methylheptyl, 5-methylheptyl, 4-methylhetyl, 3-methylheptyl, 2-methylheptyl, 1-methylheptyl, 7-methyloctyl, 6-methyloctyl, 5-methyloctyl, 4-methyloctyl, 3-methyloctyl, 2-metyloctyl, 1-methyloctyl, 8-methylnonyl, 7-methylnonyl, 6-methylnonyl, 5-methylnonyl, 4-methylnonyl, 3-methylnonyl, 2-methylnonyl, 1-methylnonyl, 3,7-dimethyloctyl, 3,7,11-trimethyldodecyl, and the like.

The novel compounds of this invention contains a carbonyl group within a 5-membered ring and one or two asymmetric carbon atoms on the ring as a moiety having a dipole moment a an origin of ferroelectricity, and hence, the free rotation at this moiety is inhibited and thereby the dipole moiety is directed to one direction, which is effective for enlarging the spontaneous polarization and for increasing the response speed. In the liquid crystalline compounds (A) of this invention, when $R^2$ is hydrogen atom, only one asymmetric carbon atom is contained, but when $R^2$ is a group other than hydrogen, two asymmetric carbon atoms are contained in the γ-lactone ring and hence there are present two kinds of diastereomer. These are all suitable for inhibition of free rotation of the dipole moiety, and they are used as a liquid crystal alone or in a mixture of two or more thereof.

The compounds (A) of the invention can be prepared by a process which comprises reacting an optically active glycidyl ether of the formula:

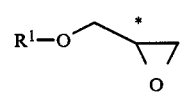 (B)

wherein $R^1$ and the symbol * are the same as $R^1$ and * in the formula (A), with a b-ketoester or malonate of the formula, respectively

 (C)

or

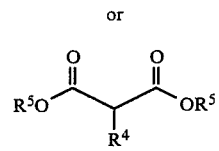 (D)

wherein $R^4$ is hydrogen atom or an alkyl group having 1 to 15 carbon atoms and $R^5$ is a lower alkyl group having 1 to 4 carbon atoms, in the presence of a base in an organic The starting optically active glycidyl ether (B) can be prepared by a process as shown in the following reaction scheme:

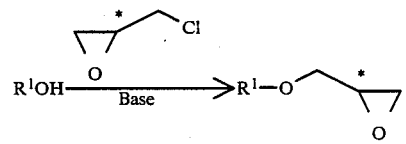

wherein $R^1$ and the symbol * are the same as $R^1$ and * in the formula (A).

That is, a phenol derivative of the formula $R^1OH$ is reacted with an optically active epichlorohydrin in the presence of a base. The optically active epichlorohydrin is preferably used in an amount of 1 to 10 equivalents to the phenol derivative, and the base is preferably used in an amount of 1 to 5 equivalents to the phenol derivative. The base includes alkali metal hydroxides or alkoxides, such as sodium hydroxide, potassium hydroxide, potassium t-butoxide, and the like. The above reaction may proceed smoothly without any catalyst, but may be carried out in the presence of a catalyst. The catalyst includes quaternary ammonium halides, such as benzyltriethylammonium chloride, benzyltriethylammonium bromide, benzyltrimethylammonium chloride, benzyltrimethylammonium bromide, etc. and is used in an amount of 0.01 to 0.1 equivalent to the phenol derivative. An excess amount of the optically active epichlorohydrin may be used as the solvent, but there is preferably used a suitable polar solvent such as dimethylformamide, dimethylsulfoxide, dimethylacetamide, acetonitrile, t-butyl alcohol, and water. The reaction is usually carried out at a temperature of 50° to 80° C. for 0.5 to 3 hours.

Alternatively, the optically active glycidyl ether (B) may also be prepared by reacting the phenol derivative of the formula $R^1OH$ with an optically active epichlorohydrin in the presence of an amine (e.g. morpholine, piperidine, pyridine, etc.) of 0.1 to 0.5 equivalent to the phenol derivative and subjecting the resulting optically active chlorohydrin derivative to cyclization reaction with 1 to 5 equivalents of a base, such as an alkali metal hydroxide, carbonate or alkoxide (e.g. sodium hydroxide, potassium hydroxide, potassium carbonate, sodium carbonate, potassium t-butoxide, etc.). The latter process is carried out in two steps but is advantageous in that the extraction of the product can easily be done. This reaction is usually carried out at a temperature of 50 to 80° C. for 3 to 24 hours.

When a racemic epichlorohydrin is used in the above reaction, there is obtained a glycidyl ether in the form of a racemic mixture. The starting optically active epicllorohydrin can be prepared in a high purity by the processes as described in Japanese Patent First Publication (Kokai) Nos. 132196/1986 and 669/1987 (as to R isomer) and by the process as described in Japanese Patent Application No. 283393/1987 (as to S isomer).

Besides, the starting phenol derivative used for the preparation of the compound (B) can be prepared by the processes as shown in the following Reaction Schemes-I to -VI, wherein $R^3$ is the same as $R^3$ in the formula (A), $R^{3'}$ is hydrogen atom or an alkyl group having a carbon atom one smaller than that in $R^3$, Ph means phenyl, and R' is a lower alkyl group having 1 to 4 carbon atoms.

That is, 4-(4-trans-alkylcyclohexyl)phenols, 4-(4-alkyloxyphenyl)phenols, and 4-(4-alkylphenyl)phenols are prepared by the known processes as shown in Reaction Schemes-I, -II and -III, respectively.

Reaction Scheme-I

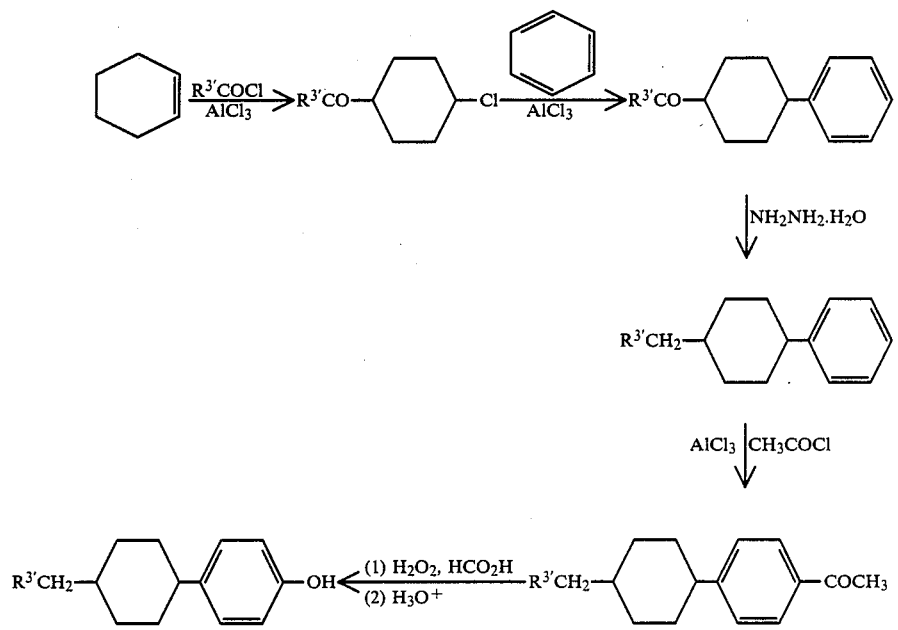

Reaction Scheme-II

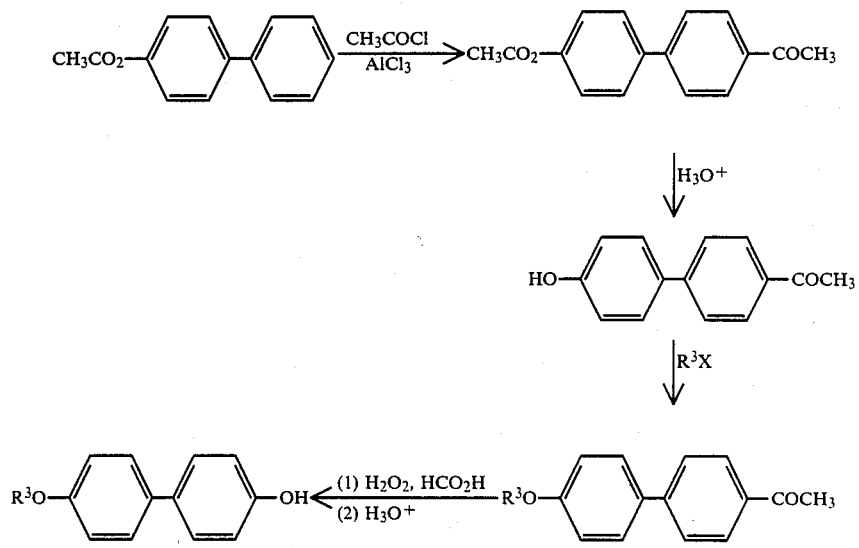

Reaction Scheme-III
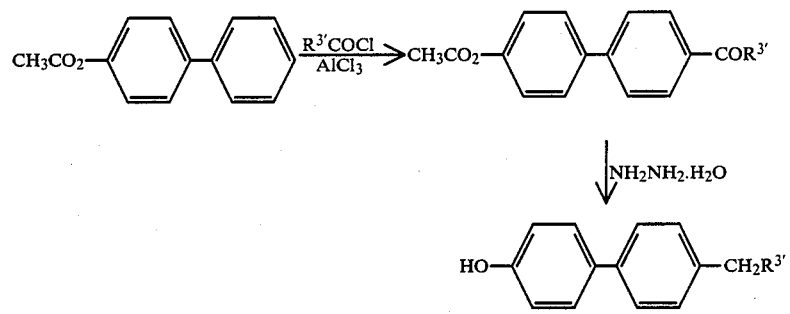
Besides, 4-(5-alkyl-2-pyrimidinyl)phenols and 4-(5-alkyloxy-2-pyrimidinyl)phenols are prepared by the processes as shown in the following Reaction Schemes-IV and -V, respectively, which are disclosed in Japanese Patent First Publication (Kokai) Nos. 189274/1986 and DE 144,409.
Reaction Scheme-IV
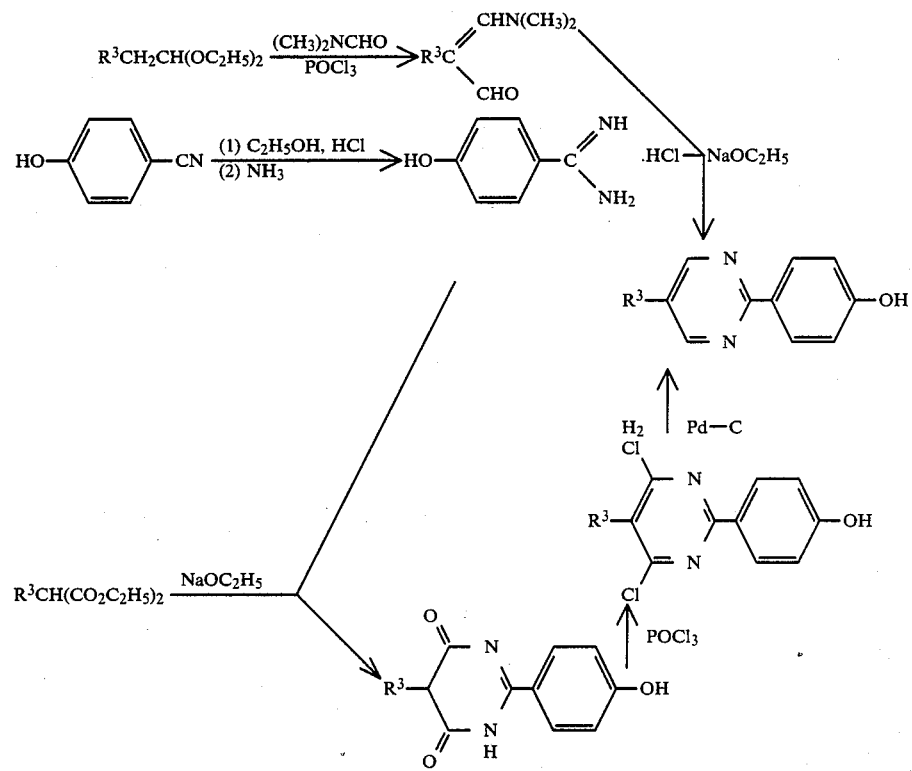
Reaction Scheme-V
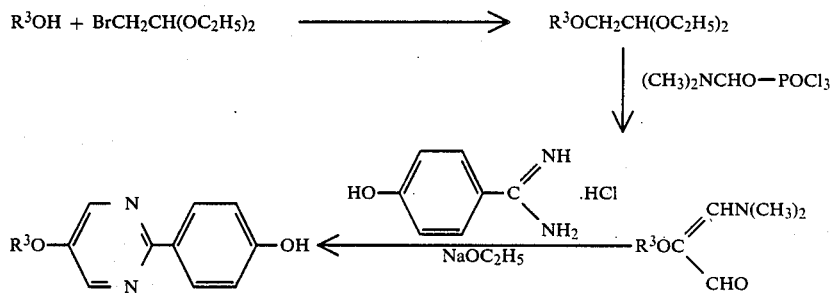

Moreover, 4-[5-(4-alkyloxyphenyl)-2-pyrimidinyl]phenols and 4-[5-(4-alkylphenyl)-2-pyrimidinyl]phenols are prepared by the processes as shown in the following Reaction Scheme-VI.

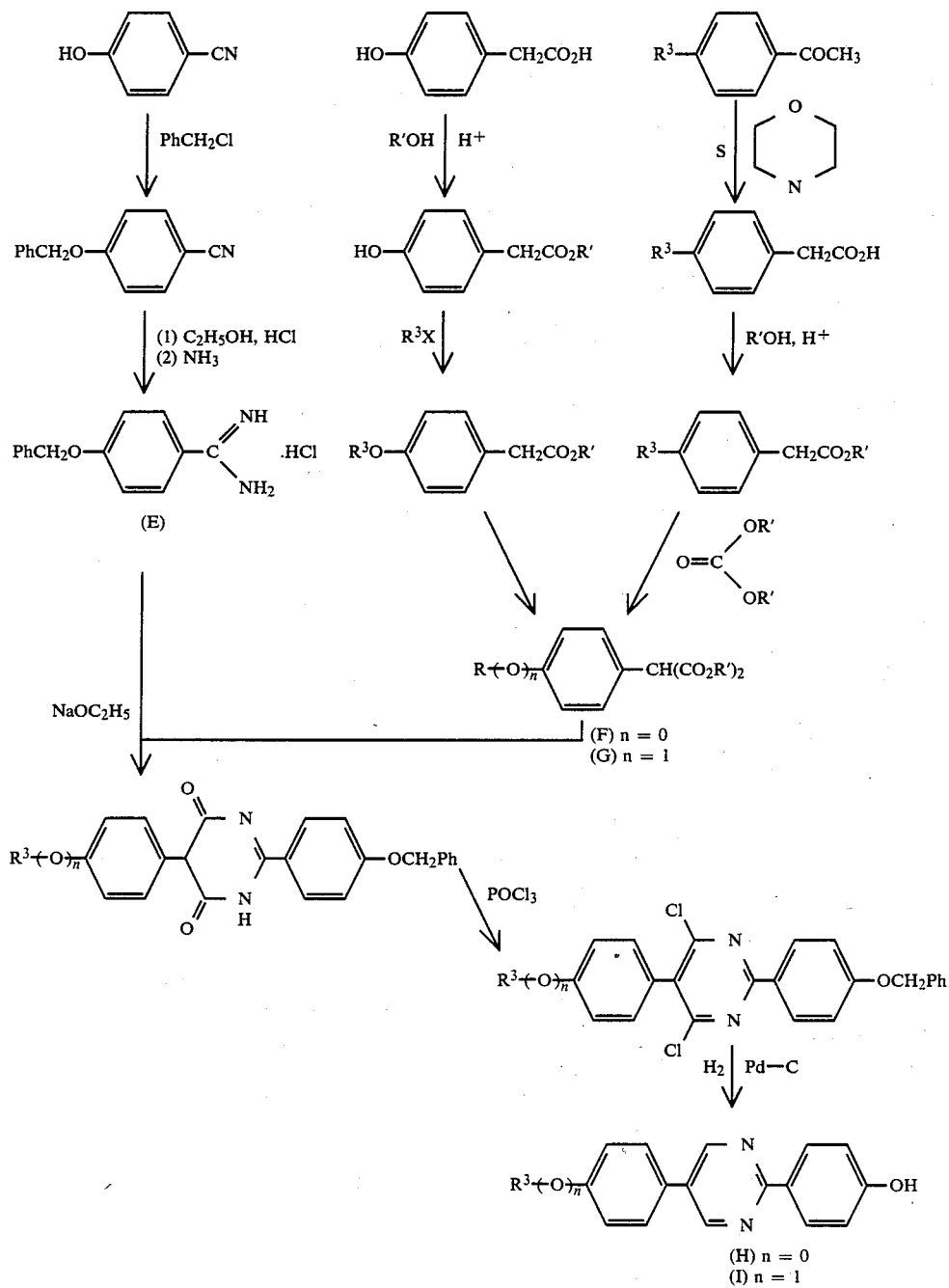

According to the process of Reaction Scheme-VI, Compound (E) is prepared by protecting hydroxy group of p-hydroxybenzonitrile with benzyl group and converting the cyano group thereof into amidine hydrochloride in a usual manner. Separately, p-hydroyphenylacetic acid is esterified with a lower alcohol, and the phenolic hydoxy group is alkylted with an alkyl halide, alkyl p-toluenesulfonate or alkyl methanesulfonate, followed by reacting with diethyl carbonate in the presence of a base to give diethyl malonate derivative (G).

The amidine hydrochloride (E) is condensed with the diethyl malonate derivative (G) in the presence of a base such as alkali metal alkoxides (e.g. sodium ethoxide, sodium methoxide, etc.), followed by reacting with phosphorus oxychloride in the presence of a base such as organic amines (e.g. N,N-diethylaniline, pyridine, 4-(N,N-dimethylamino)pyridine, etc.), and the resulting compound is reduced with hydrogen gas in the presence of Pd-C catalyst to give the desired 4-[5-(4-alkyloxyphenyl)-2-pyrimidinyl]phenol (I).

In the above process, when a diethyl p-alkylphenylmalonate (F) is used instead of the diethyl malonate derivative (G) and the compound (E) and the compound (F) are reacted like in the reaction of the compound (E) and the compound (G), there is prepared 4-[5-(4-alkylphenyl)-2-pyrimidinyl]phenol (H).

The diethyl p-alkylphenylmalonate (F) can be prepared by subjecting a p-alkylacetophenone to Willgerodt reaction, esterifying the resulting phenylacetic acid derivative with a lower alcohol, and condensing the resultant with diethyl carbonate.

The desired compound (A) of this invention can be prepared by reacting under reflux the compound (B) with 1 to 5 equivalents of the compound (C) or the compound (D) in the presence of 1 to 5 equivalents of a base in an organic solvent for 1.5 to 24 hours. The base used therein includes alkali metal alkoxides (e.g. sodium methoxide, sodium ethoxide, potassium t-butoxide, etc.), alkali metal hydrides (e.g. sodium hydride, lithium hydride, etc.), and alkyl alkali metals (e.g. n-butyllithium, etc.), and the organic solvent includes alcohols (e.g. methanol, ethanol, t-butyl alcohol, etc.), ethers (e.g. tetrahydrofuran, diethyl ether, dimethoxyethane, diethylene glycol dimethyl ether, dioxane, etc.), aprotic polar solvents (e.g. dimethylformamide, dimethylsulfoxide, hexamethylphosphoric triamide, etc.), and a mixture of these solvents.

In the above process, when $R^4$ in the compound (D) is hydrogen atom, the final compound prepared by the process is mixed with an inorganic salt (1 to 10 equivalents) and water under neutral condition and then is refluxed in a polar solvent to give the desired compound (A). The solvent used therein includes polar solvents such as dimethylformamide, dimethylacetamide, dimethylsulfoxide, hexamethylphosphoric triamide, diethylene glycol dimethyl ether, dioxane, and the like. The inorganic salt includes alkali metal or alkaline earth metal halides, such as lithium chloride, sodium chloride, potassium chloride, lithium bromide, sodium bromide, potassium bromide, lithium iodide, sodium iodide, potassium iodide, magnesium chloride, calcium chloride, strontium chloride, barium chloride, magnesium bromide, calcium bromide, barium bromide, magnesium iodide, calcium iodide, barium iodide, and the like. Water is preferably used in an amount of 5 to 50 equivalents. The reaction is completed in 1 to 15 hours.

The liquid crystalline compounds of this invention may be obtained in the form of a racemic mixture when a racemic epichlorohydrin is used as the starting material, and the racemic compounds may be added to other optically active liquid crystalline compounds in order to regulate the helical pitch thereof. The liquid crystalline compounds of this invention have excellent heat stability and light stability, and the optically active compounds have excellent properties as ferroelectric liquid crystal. The liquid crystalline compounds of this invention are also useful for the following utilities.

(1) Additives for TN (Twisted Nematic) type or STN (Super Twisted Nematic) type liquid crystals in order to inhibit occurrence of reverse domain.

(2) Display element utilizing cholesteric - nematic phase transfer effects (cf. J. J. Wysoki, A. Adams and W. Haas; Phys. Rev. Lett., 20, 1024, 1968).

(3) Display element utilizing White-Taylor type guest host effects (cf. D. L. White and G. N. Taylor; J. Appl. Phys., 45, 4788, 1974).

(4) Notch filter or band-pass filter utilizing selective scattering effects by fixing the cholesteric phase in matrix (cf. F. J. Kahn; Appl Phys. Lett., 18, 231, 1971).

(5) Circularly polarized light beam splitter utilizing circularly polarized light characteristics of the cholesteric phase (cf. S. D. Jacob: SPIE. 37, 98, 1981).

This invention is illustrated by the following Preparations and Examples, but should not be construed to be limited thereto.

In Examples, the positions of R and S in the optically active compounds (A) of this invention are shown by the position numbers in the following formula:

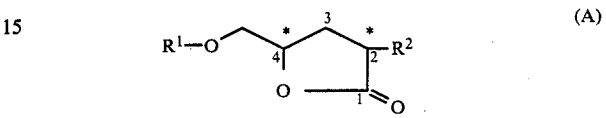

The phase transfer temperature in Examples was measured by DSC (Differential Scanning Colorimetry) and a polarizing microscope. Besides, the symbols in the phase transfer temperature mean as follows:

C: Crystalline phase
SmA: Smectic A phase
SmC: Smectic C phase
SmC*: Chiral smectic C phase
SmI: Non-identified smectic phase other than SmA, SmC and SmC*.
N: Nematic phase
N*: Chiral nematic phase
I: Isotropic liquid The chiral smectic C phase (SmC*) was further confirmed by measuring the dielectric constant thereof.

[Preparation of phenol derivatives]

PREPARATION 1

Preparation of 4-[5-(4-n-octyloxyphenyl)-2-pyrimidinyl]phenol (i) Preparation of 4-benzyloxyphenylamidine hydrochloride:

4-Cyanophenol (95.2 g), benzyl chloride (127 g) and potassium carbonate (138 g) are refluxed in acetone (160 ml) for 5 hours. The product is separated by filtration, concentrated under reduced pressure, and thereto is added benzene. The mixture is washed with water, and benzene is distilled off under reduced pressure to give 4-benzyloxybenzonitrile (141.38 g). The 4-benzyloxybenzonitrile (141 g) is dissolved in benzene (338 ml) and thereto is added ethanol (270 ml), and the mixture is cooled to 0° C. Into the resulting slurry is bubbled hydrogen chloride gas (36 liters) with stirring, and thereafter, the temperature is raised to 25° C., and the mixture is allowed to stand for 2 days. The reaction mixture is concentrated under reduced pressure until ⅓ volume, and to the concentrated mixture is added ether. The precipitated crystals are separated by suction filtration to give an imide ester (183 g).

The above-obtained imide ester (183 g) is mixed with ethanol (270 ml) to give a slurry, and thereto is added a solution of ammonia (60.75 g) in ethanol (405 ml). After allowing the mixture to stand at room temperature for 2 days, the solvent is distilled off under reduced pressure to give 4-benzyloxyphenylamidine hydrochloride (164.5 g). NMR (DMSO-$d_6$) δ: 5.19 (2H, s), 7.17 (2H, d, J=9.0 Hz), 7.35 (5H, s), 7.86 (2H, d)

(ii) Preparation of diethyl 4-n-octyloxyphenylmalonate:

4-Hydroxyphenylacetic acid (50.0 g) is dissolved in ethanol (400 ml) and thereto is added conc. sulfuric acid (0.5 ml). The mixture is refluxed with stirring, and ethanol is distilled off to give ethyl 4-hydroxyphenylacetate (60 g).

The ethyl 4-hydroxyphenylacetate (59 g) and sodium ethoxide (22.4 g) are dissolved in ethanol (150 ml) and thereto is added n-octyl bromide (63.5 g), and the mixture is refluxed for 3 hours and concentrated under reduced pressure, and thereto is added ethyl acetate to dissolve the oily substance. The mixture is washed with water, dried over anhydrous magneisum sulfate, distilled under reduced pressure to remove ethyl acetate, and further distilled under reduced pressure to give ethyl 4-n-octyloxyphenylacetate (79.6 g, b.p. 179° C./0.1 mmHg).

The obtained ethyl 4-n-octyloxyphenylacetate (79 g), ethanol (14 ml), diethyl carbonate (300 ml) and sodium ethoxide (19.3 g) are mixed, and the mixture is heated with stirring while ethanol is distilling off. The reaction mixture is transferred into ice water and is acidified with hydrochloric acid. The organic layer is separated and the solvent is distilled off to give diethyl 4-n-octyloxyphenylmalonate (91.6 g).

NMR (CDCl$_3$) δ: 0.5-2.0 (21H, m), 3.90 (2H,t, J=6.0 Hz), 4.16 (4H, q, J=7.2 Hz). 4.52 (1H, s), 6.80 (2H, d, J=9.0 Hz), 7.2 (2H, d, J=9.0 Hz)

(iii) Preparation of 4-[5-(4-n-octyloxyphenyl)-2-pyrimidinyl]phenol:

4-Benzyloxyphenylamidine hydrochloride (65.6 g) and diethyl 4-n-octyloxyphenylmalonate (91.0 g) are dissolved in methanol (500 ml) and thereto is added sodium methoxide (44.8 g), and the mixture is refluxed with stirring for 9 hours. After cooling, the reaction mixture is acidified with sulfuric acid, and the precipitated crystals are separated by suction filtration to give yellow crystals (77.7 g).

The above yellow crystals (77 g), phosphorus oxychloride (310 ml) and N,N-diethylaniline (46.5 ml) are mixed and refluxed with stirring for 26 hours. The excess phosphorus oxychloride is distilled off under reduced pressure, and the residue is transferred into icewater and extracted with ether. The extract is washed with water and distilled to remove ether to give a crude product (70 g). The product is recrystallized from ether to give a compound (21 g) of the following formula:

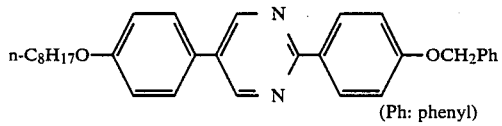

(Ph: phenyl)

NMR (CDCl$_3$) δ: 0.4–2.1 (15H, m), 3.99 (2H, t, J=6.0 Hz), 5.09 (2H, s), 6.7–7.5 (11H, m), 8.38 (2H, d, J=9.0 Hz)

The colorless crystals obtained above (19.8 g), ethanol (757 ml), magnesium oxide (11.4 g), water (57 ml) and 1% Pd-C (4 g) are heated with stirring at 60° C. under hydrogen atmosphere until a theoretical amount of hydrogen is absorbed. The reaction mixture is filtered with suction, and the filtrate is concentrated to give the desired 4-[5-(4-n-octyloxyphenyl)-2-pyrimidinyl]phenol (7.7 g), m.p. 137° C.

NMR (CDCl$_3$) δ: 0.5–2.1 (15H, m), 4.00 (2H, t, J=6.0 Hz), 6.92 (2H, d, J=9.0 Hz), 7.01 (2H, d, J=9.0 Hz), 7.50 (2H, d, J=9.0 Hz), 8.30 (2H, d, J=9.0 Hz), 8.94 (2H, s)

[Preparation of the compounds (B)]

The starting optically active epichlorohydrins are prepared by the processes as disclosed in Japanese Patent First Publication (Kokai) Nos. 132196/1986 and 6697/1987 and in Japanese Patent Application No. 283393/1987. These are R-(—)- and S-(+)-epichlorohydrins which have a chemical purity of 98.5% or more (measured by gas chromatographic analysis) and an optical purity of 99% or more [the specific rotation, $[\alpha]_D^{25} = -34.0°$, $+34.0°$, c $=1.2$, methanol, respectively].

PREPARATION 2

To a mixture of the above R-(—)-epichlorohydrin (5.55 g), 4-(trans-4-n-pentylcyclohexyl)phenol (2.46 g) of the following formula:

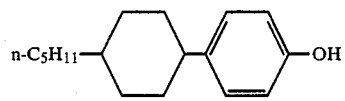

and benzyltriethylammonium chloride (0.04 g) is added dropwise aqueous sodium hydroxide (NaOH 0.45 g, water 15 ml) with stirring at 60° C. over a period of 20 minutes, and the mixture is further refluxed for one hour. The reaction mixture is cooled to room temperature and extracted twice with ether. The extract is washed once with a saturated saline solution and distilled under reduced pressure to remove the solvent. The residue is purified by silica gel chromatography to give (S)-2,3-epoxypropyl 4-(trans-4-n-pentylcyclohexyl)phenyl ether (1.8 g) of the following formula:

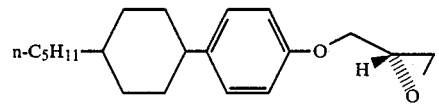

$[\alpha]_D^{25} = +4.44°$ (c=1.36, CH$_2$Cl$_2$)

NMR (CDCl$_3$) δ: 0.45–2.50 (21H, m), 2.50–3.00 (2H, m), 3.15–3.50 (1H, m), 3.70–4.30 (2H, m), 6.79 (2H, d, J=9.0 Hz), 7.09 (2H, d, J=9.0 Hz)

PREPARATION 3

The starting phenol derivative (2.50 g) of the following formula:

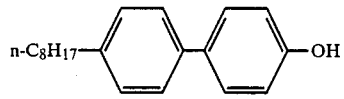

and the same R-(—)-epichlorohydrin (4.25 g) and benzyltriethylammonium chloride (20 mg) as used in Preparation 2 are dissolved in dimethylformamide (3 ml) and thereto is added dropwise 24 wt. % aqueous sodium hydroxide (1.2 equivalent) at 60° C. After reacting at the same temperature for 40 minutes, the reaction mixture is cooled to room temperature and extracted with ether. The extract is distilled under reduced pressure to remove the solvent. The residue is purified by silica gel chromatography to give S isomer of glycidyl ether (1.62 g) of the following formula:

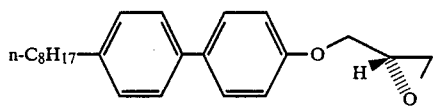

m.p. 90° C.
$[\alpha]_D^{25} = +4.44°$ (c=1.01, CH$_2$Cl$_2$)
NMR (CDCl$_3$) δ: 0.50–3.00 (19H, m), 3.10–3.50 (1H, m), 3.80–4.30 (2H, m), 6.75–7.60 (8H, m)

PREPARATION 4

The starting phenol derivative 10.0 g) of the following formula:

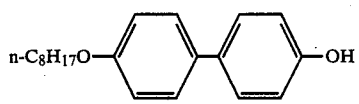

and the same R-(−)-epichlorohydrin (18.6 g) as used in Preparation 2, piperidine (367 ml) and dimethylformamide (1 ml) are mixed and stirred at 60° C. for 10 hours. The reaction mixture is distilled under reduced pressure to remove the solvent, and thereto is added acetone (5 ml) and further added dropwise 24 wt. % aqueous sodium hydroxide (1.2 equivalent) with stirring at room temperature, and the mixture is reacted for 30 minutes. The reaction mixture is adjusted to pH 7 with 2N hydrochloric acid and extracted with ethyl acetate. The extract is dried over anhydrous magnesium sulfate and distilled under reduced pressure to remove the solvent. The residue is purified by silica gel chromatography to give S isomer of glycidyl ether (1.58 g) of the following formula:

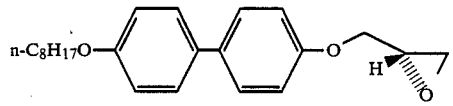

m.p. 131° C.
$[\alpha]_D^{27} = +3.03°$ (c=0.55, CH$_2$Cl$_2$)
NMR (CDCl$_3$) δ: 0.70–2.20 (17H, m), 2.55–3.00 (2H, m), 3.15–3.45 (1H, m), 3.75–4.20 (2H, m), 6.89 (2H, d, J=9.0 Hz), 6.92 (2H, d, J=8.4 Hz), 7.43 (4H, d, J=9.0 Hz)

PREPARATION 5

A phenol derivative (5.28 g) of the following formula:

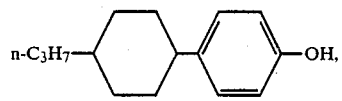

S-(+)-epichlorohydrin (11.55 g), potassium t-butoxide (3.00 g) and t-butyl alcohol (45 ml) are mixed, the mixture is stirred at 60° C. for 3 hours. The reaction mixture is distilled under reduced pressure to remove the solvent and the residue is extracted with chloroform. The extract is distilled under reduced pressure to remove the solvent. The residue is purified by silica gel chromatography to give R isomer of glycidyl ether(5.82 g) of the following formula:

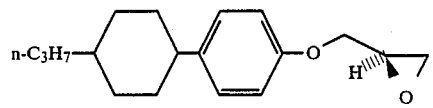

$[\alpha]_D^{31} = -5.71°$ (c=1.66, CH$_2$Cl$_2$)
NMR (CDCl$_3$) δ: 0.60–2.50 (17H, m), 2.60–2.95 (2H, m), 3.15–3.60 (1H, m), 3.80–4.30 (2H, m), 6.76 (2H, d, J=8.4 Hz), 7.07 (2H, d, J=8.4 Hz)

PREPARATION 6

In the same manner as described in Preparation 5 except that a compound of the following formula:

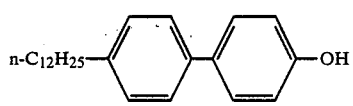

is used as the starting phenol derivative, there is prepared R isomer of glycidyl ether of the following formula:

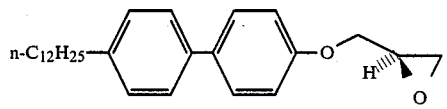

m.p. 91° C.
$[\alpha]_D^{35} = -3.59°$ (c=1.07, CH$_2$Cl$_2$)
NMR (CDCl$_3$) δ: 0.85–2.93 (27H, m), 3.34–3.40 (1H, m), 3.97–4.27 (2H, m), 6.94–7.53 (8H, m)

PREPARATION 7

A mixture of the starting phenol derivative (10 g) of the following formula:

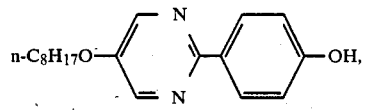

the same R-(−)-epichlorohydrin (16.07 g) as used in Preparation 2, 20 wt. % aqueous sodium hydroxide (7.33 g) and dimethylformamide (20 ml) is heated with stirring at 60°–70° C. for one hour. The reaction mixture is cooled and thereto is added water. The mixture is extracted with chloroform to obtain a crude product (11.67 g). The crude product is purified by silica gel chromatography to give S isomer of glycidyl ether (9.07 g) of the following formula:

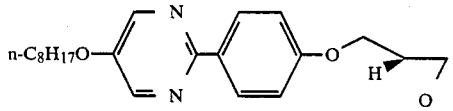

m.p. 74° C.
$[\alpha]_D^{24} = +1.66°$ (c=1.02, CH$_2$Cl$_2$)

NMR (CDCl₃) δ: 0.5–2.2 (15H, m), 2.6–3.0 (2H, m), 3.1–3.7 (1H, m), 3.8–4.4 (4H, m), 6.95 (2H, d, J=9.0 Hz), 8.26 (2H, d, J=9.0 Hz), 8.36 (2H, s)

PREPARATION 8

A mixture of the starting phenol derivative (7.44 g) of the following formula:

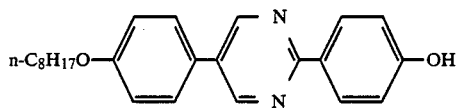

as prepared in Preparation 1, the same R-(—)-epichlorohydrin (9.16 g) as used in Preparation 2, 50 wt. % aqueous sodium hydroxide (1.74 g) and dimethylformamide (77 ml) is stirred at 60°–70° C. for 3 hours. The reaction mixture is cooled and thereto is added water, and the mixture is extracted with dichloromethane. The extracted product is purified by silica gel chromatography to give S isomer of glycidyl ether (6.90 g) of the following formula:

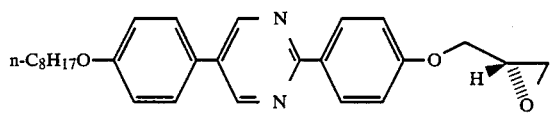

m.p. 198° C.
[α]$_D^{25}$ = +0.95° (c=1.04, CH₂Cl₂)
NMR (CDCl₃) δ: 0.6–2.1 (15H, m), 2.6–3.0 (2H, m), 3.2–3.5 (1H, m), 3.8–4.5 (2H, m), 6.99 (4H, d, J=9.0 Hz), 7.50 (2H, d, J=9.0 Hz), 8.40 (2H, d, J=9.0 Hz), 8.90 (2H, s)

PREPARATION 9

The starting phenol derivative (1.01 g) of the following formula:

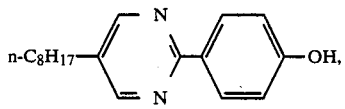

the same R-(—)-epichlorohydrin (2.01 g) as used in Preparation 2 and benzyltriethylammonium chloride (16 mg) are mixed and heated at 70° C., and thereto is added dropwise 24 wt. % aqueous sodium hydroxide (650 mg). The mixture is stirred at 70° C. for 2 hours. The reaction mixture is cooled to room temperature and extracted three times with chloroform. The extract is dried over anhydrous magnesium sulfate and distilled under reduced pressure to remove the solvent. The residue is recrystallized from hexane to give S isomer of glycidyl ether (380 mg) of the following formula:

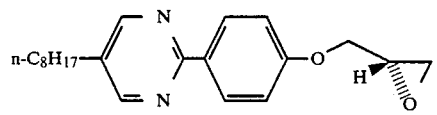

m.p. 65° C.
[α]$_D^{25}$ = +1.90° (c=0.46, CH₂Cl₂)

NMR (CDCl₃) δ: 0.6–3.0 (19H, m), 3.2–3.6 (1H, m) 3.9–4.5 (2H, m), 6.99 (2H, d, J=9.0 Hz), 8.36 (2H, d, J=9.0 Hz), 8.55 (2H, s)

PREPARATION 10

A mixture of the starting phenol derivative (3.12 g) of the following formula:

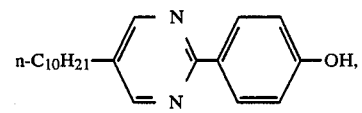

the same R-(—)-epichlorohydrin (4.627 g) as used in Preparation 2, 50 wt. % aqueous sodium hydroxide (0.88 g) and dimethylformamide (30 ml) is heated with stirring at 60° C. for 2.5 hours. The reaction mixture is cooled and distilled under reduced pressure to remove the solvent. The product is purified by silica gel chromatography to give S isomer of glycidyl ether (2.96 g) of the following formula:

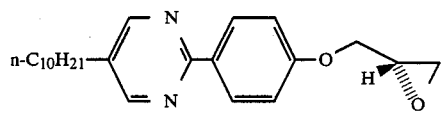

m.p. 65° C.
[α]$_D^{27}$ = +2.47° (c=1.02, CH₂Cl₂)
NMR (CDCl₃) δ: 0.6–2.0 (19H, m), 2.4–3.0 (4H, m), 3.2–3.5 (1H, m), 3.8–4.5 (2H, m), 6.98 (2H, d, J=9.0 Hz), 8.33 (2H, d, J=9.0 Hz), 8.53 (2H, s)

PREPARATION 11–12

In the same manner as described in Preparations 2–10, there are prepared optically active glycidyl ethers as shown in Table 1, wherein R³, n, X and the symbol * are of the following formula:

TABLE 1

$$R^3-(O)_n-X-O-CH_2-\overset{*}{CH}-CH_2$$

| No. | R³ | n | X | * | [α]$_D$ |
|---|---|---|---|---|---|
| 11 | n-C₆H₁₃ | 0 | —⟨phenyl⟩—⟨phenyl⟩— | S | +4.78° (c = 1.08, CH₂Cl₂, 30° C.) |
| 12 | n-C₉H₁₉ | 0 | —⟨cyclohexyl⟩—⟨phenyl⟩— | S | +3.86° (c = 1.06, CH₂Cl₂, 31° C.) |

[Preparation of Compound (A)]

EXAMPLE 1

A dispersion of 50 wt. % sodium hydride (224 mg) in mineral oil is washed twice with dry ether and thereto is added dry tetrahydrofuran (10 ml). To the mixture is added dropwise methyl 3-oxododecanate (1.07 g) with stirring at 40° C. After stirring the mixture for 5 minutes, (S)-2,3-epoxypropyl 4-(trans-4-n-pentylcyclohexyl)phenyl ether (1.41 g) as prepared in Preparation 2 is added dropwise to the reaction mixture, and the mixture is refluxed for 20 hours. The reaction mixture is cooled to room temperature and thereto is added dropwise 4N hydrochloric acid until pH 1. The mixture is extracted twice with ether, and the extract is washed once with a saturated saline solution and distilled under reduced pressure to remove the solvent. The residue is purified by silica gel chromatography to give γ-lactone derivatives (A) (430 mg, as a mixture of (2S, 4S) isomer : (2R, 4S) isomer=50 : 50) of the following formulae:

(2R, 4S) isomer:

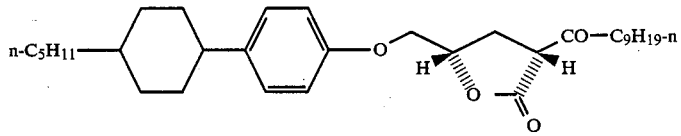

(2S, 4S) isomer:

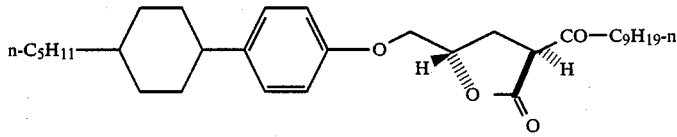

NMR (CDCl$_3$) δ: 0.87–1.86 (39H, m), 2.26–3.06(3H, m), 3.73–4.21 (3H, m), 4.85–4.90 (1H, m), 6.82 (2H, d, J=8.54 Hz), 7.12 (2H, d, J=8.55 Hz)

IR (KBr): 1778, 1720 cm$^{-1}$ $[\alpha]_D^{29} = +18.1°$ (c=1.06, (CHCl$_3$)

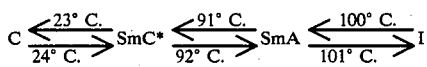

The γ-lactone derivatives prepared in the above Example 1 were sealed in a cell made of glass wherein a polyethylene terephthalate film (thickness 50 μm was used as a spacer. The cell was charged with alternating current of 70 Hz, and the relative dielectric constant was measured by bridge method. The results are shown in the accompanying FIG. 1. It is clear from the test results that these compounds have ferroelectric property.

EXAMPLE 2

In the same manner as described in Example 1 except that methyl 3-oxononanate (1.14 g) is used instead of methyl 3-oxododecanate, it is reacted with (S)-2,3-epoxypropyl 4-(trans-4-n-pentylcyclohexyl)phenyl ether as prepared in Preparation 2 to give γ-lactone derivatives (A) (970 mg, as a mixture of (2S, 4S) isomer : (2R, 4S) isomer=50 : 50) of the following formulae:

(2R, 4S) isomer:

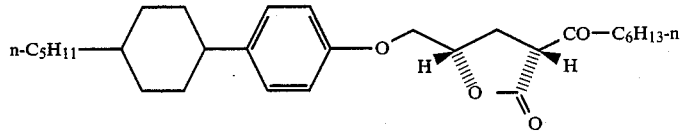

(2S, 4S) isomer:

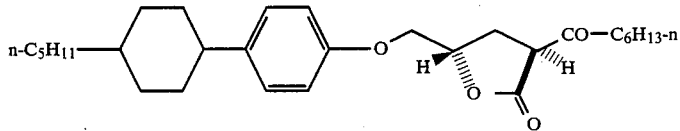

NMR (CDCl$_3$) δ: 0.87–1.88 (33H, m), 2.20–3.09 (3H, m), 3.72–4.21 (3H, m), 4.77–4.99 (1H,m), 6.81 (2H, d, J=8.55 Hz), 7.10 (2H, d, J=8.55 Hz)

IR (KBr): 1762, 1716 cm$^{-1}$ $[\alpha]_D^{29} = +13.3°$ (c=1.09, (CHCl$_3$)

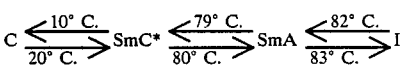

EXAMPLE 3

A dispersion of 50 wt. % sodium hydride (224 mg) in mineral oil is washed twice with dry ether and thereto is added dry tetrahydrofuran (10 ml). To the suspension is added dropwise dimethyl n-butylmalonate (130 mg) with stirring at 40° C. After stirring the mixture for 5 minutes, (S)-2,3-epoxypropyl 4-(trans-4-n-pentylcyclohexyl)phenyl ether (1.41 g) as prepared in Preparation 2 is added dropwise to the mixture, and the mixture is refluxed with stirring for 20 hours. The reaction mixture is cooled to room temperature and thereto is added dropwise 4N hydrochloric acid until pH 1. The mixture is extracted twice with ether, and the extract is washed once with a saturated saline solution and distilled under reduced pressure to remove the solvent. The residue is purified by silica gel chromatography to give γ-lactone derivatives, 2S, 4S) isomer and (2R, 4S) isomer (50 mg and 40 mg, respectively) of the following formulae:

(2S, 4S) isomer:

-continued

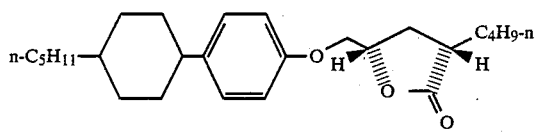

Phase transfer temperature: C $\xrightarrow{84° C.}$ I $[\alpha]_D^{23} = +33.45°$ (c=0.658, CH$_2$Cl$_2$)

NMR (CDCl$_3$) δ: 0.88–1.98 (3OH, m), 2.38–2.67 (3H, m), 4.07–4.13 (2H, m), 4.67–4.73 (1H, m), 6.83 (2H, d, J=8.3 Hz), 7.12 (2H, d, J=8.3 Hz)

IR (KBr): 1762 cm$^{-1}$

Elementary analysis for C$_{26}$H$_{40}$O$_3$: Calcd. (%): C,77.95; H,10.07. Found (%): C,7.91; H,10.12.

(2R, 4S) isomer:

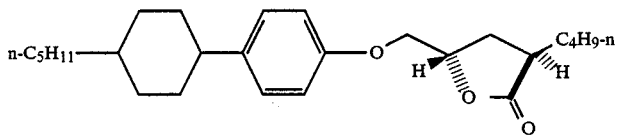

Phase transfer temperature: C $\xrightarrow{85° C.}$ I $[\alpha]_D^{24} = +20.37°$ (c=1.05, CH$_2$Cl$_2$)

NMR (CDCl$_3$) δ: 0.70–2.95 (33H, m), 4.00–4.25 (2H, m), 4.50–4.95 (1H, m), 6.77 (2H, d, J=8.4 Hz), 7.11 (2H, d, J=8.4 Hz)

IR (KBr): 1762 cm$^{-1}$

EXAMPLE 4

To a dispersion of 50 wt. % sodium hydride (163 mg) in mineral oil is added dry 1,2-dimethoxyethane (3 ml), and thereto is added dropwise a solution of dimethyl n-heptylmalonate (716 mg) in 1,2-dimethoxyethane (3 ml) with stirring at room temperature over a period of 10 minutes. After stirring the mixture for 5 minutes, a solution of (S) -2,3-epoxypropyl 4-(trans-4-n-pentylcyclohexyl)phenyl ether (940 mg) as prepared in Preparation 2 in 1,2-dimethoxyethane (4 ml) is added dropwise to the mixture over a period of 10 minutes, and the mixture is refluxed with stirring for 2.5 hours. The reaction mixture is cooled to room temperature and thereto is added dropwise 4N hydrochloric acid until pH 1. The mixture is extracted twice with ether, and the extract is washed once with a saturated saline solution and distilled under reduced pressure to remove the solvent. The residue is purified by silica gel chromatography to give a γ-lactone derivative, (2S, 4S) isomer (130 mg) of the following formula:

(2S, 4S) isomer:

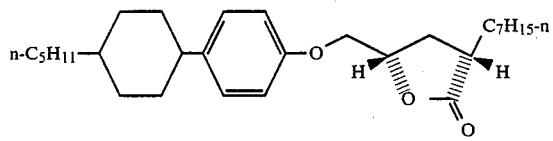

Phase transfer temperature:

-continued

C $\xrightarrow{110° C.}$ I $[\alpha]_D^{25} = +27.61°$ (c=0.039, CH$_2$Cl$_2$)

NMR (CDCl$_3$) δ: 0.78–2.82 (39H, m), 3.97–4.19 (2H, m), 4.40–4.82 (1H, m), 6.77 (2H, d, J=8.4 Hz), 7.08 (2H, d, J=8.4 Hz)

IR (KBr): 1758 cm$^{-1}$

EXAMPLE 5

The optically active glycidyl ether prepared in Preparation 2, i.e. (S)-2,3-epoxypropyl 4-(trans-4-n-pentylcyclohexyl)phenyl ether (370 mg), potassium t-butoxide (151 mg), dimethyl methylmalonate (357 mg) and t-butyl alcohol (3 ml) are mixed, and the mixture is refluxed with stirring for 8 hours. The reaction mixture is cooled to room temperature and thereto is added dropwise 4N hydrochloric acid until pH 1. The mixture is extracted twice with ether, and the extract is washed once with a saturated saline solution and distilled under reduced pressure to remove the solvent. The residue is purified by silica gel chromatography to give γ-lactone derivatives, (2S, 4S) isomer and (2R, 4S) isomer (60 mg and 5 mg, respectively) of the following formulae:

(2S, 4S) isomer:

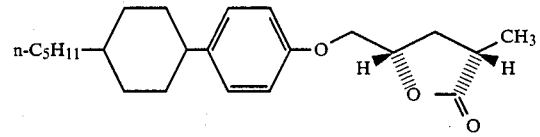

Phase transfer temperature:

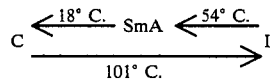

$[\alpha]_D^{27} = +14.03°$ (c=0.493, CH$_2$Cl$_2$)

NMR (CDCl$_3$) δ: 0.88 (3H, t, J=7.0 Hz), 0.97–1.84 (21H, m), 2.39 (1H, t, J=12.2 Hz), 2.49–2.56 (1H, m), 2.69–2.76 (1H, m), 4.04–4.12 (2H,m), 4.65–4.71 (1H, m), 6.83 (2H, d, J=8.7 Hz), 7.11 (2H, d, J=8.7 Hz)

IR (KBr): 1760 cm$^{-1}$

MS m/e (relative intensity, %): 359 [(M+1)$^+$, 26], 358 [M$^+$, 100]

Theoretical weight as C$_{23}$H$_{34}$O$_3$: Calcd.: 358.2509. Found: 358.2537.

(2R, 4S) isomer:

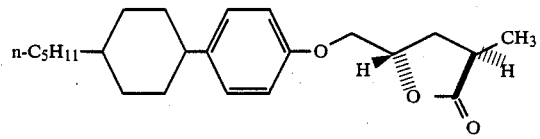

Phase transfer temperature:

$$C \xrightarrow[101° C.]{} I$$

$[\alpha]_D^{27} = +2025°$ (c=0.490, CH$_2$Cl$_2$)

NMR (CDCl$_3$) δ: 0.89 (3H, t, J=6.8 Hz), 0.97–1.40 (17H, m), 1.84 (3H, d, J=10.7 Hz), 2.02–2.10 (1H, m), 2.39 (1H, t, J=12.2 Hz), 2.45–2.51 (1H, m), 2.87–2.93 (1H, m), 4.01–4.12 (2H, m), 4.76–5.03 (1H, m), 6.79 (2H, d, J=8.6 Hz), 7.11 (2H, d, J=8.6 Hz)

IR (KBr): 1760 cm$^{-1}$

MS m/e (relative intensity, %): 359 [(M+1)$^+$, 26]358 [M$^+$, 100]

EXAMPLE 6

The optically active glycidyl ether prepared in Preparation 5, i.e. (R)-2,3-epoxypropyl 4-(trans-4-n-propylcyclohexyl)phenyl ether (416 mg), potassium t-butoxide (188 mg), dimethyl methylmalonate (443 mg) and t-butyl alcohol (2.5 ml) are mixed, and the mixture is refluxed with stirring for 2 hours. The reaction mixture is cooled to room temperature and thereto is added dropwise 4N hydrochloric acid until pH 1. The mixture is extracted three times with chloroform, and the extract is washed once with saturated saline solution and distilled under reduced pressure to remove the solvent. The residue is purified by silica gel chromatography to give γ-lactone derivatives, (2R, 4R) isomer (77 mg) and 2S, 4R) isomer (86 mg) of the following formulae:

(2R, 4R) isomer:

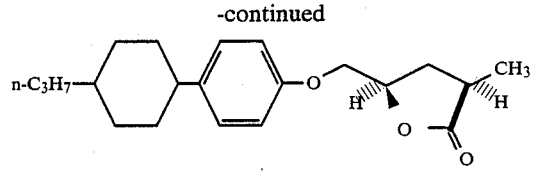

Phase transfer temperature:

$$C \xleftarrow{11° C.} SmA \xleftarrow{17° C.} I$$
$$C \xrightarrow[117° C.]{} I$$

$[\alpha]_D^{32} = -16.82°$ (c=0.98, CH$_2$Cl$_2$)

NMR (CDCl$_3$) δ: 0.6–3.0 (23H, m), 4.0–4.2 (2H, m), 4.4–4.95 (1H, m), 6.76 (2H, d, J=8.0 Hz), 7.10 (2H, d, J=8.0 Hz)

IR (KBr): 1762 cm$^{-1}$ (2S, 4R) isomer:

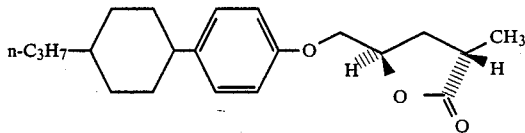

Phase transfer temperature:

$$C \xleftarrow{52° C.} I$$
$$C \xrightarrow[139° C.]{} I$$

$[\alpha]_D^{28} = -27.82°$ (c=1.03, CH$_2$Cl$_2$)

NMR (CDCl$_3$) δ: 0.65–3.0 (23H, m), 4.0–4.2 (2H, m), 4.6–5.0 (1H, m), 6.76 (2H, d, J=8.0 Hz), 7.10 (2H, d, J=8.0 Hz)

IR (KBr): 1762 cm$^{-1}$

EXAMPLES 7 to 11

In the same manner as described in Examples 1 to 6, there are prepared optically active γ-lactone derivatives as shown in Table 2, wherein R$^3$, R$^4$, n, m, and symbols 2* and 4* are of the following formula:

TABLE 2

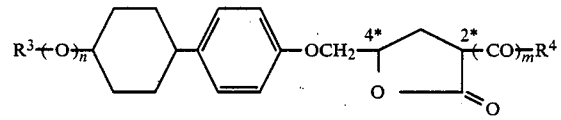

| Ex. No. | R$^3$ | n | 2* | 4* | m | R$^4$ | C | | SmI | SmC* | SmA | N* | I |
|---|---|---|---|---|---|---|---|---|---|---|---|---|---|
| 7 | n-C$_3$H$_7$ | 0 | S | R | 0 | n-C$_9$H$_{19}$ | · | $\xrightarrow[127]{}$ | — | — | — | — | · |
|  | " | " | R | R | " | " | · | $\xrightarrow[113]{}$ | — | — | — | — | · |
| 8 | n-C$_5$H$_{11}$ | " | R | S | " | C$_2$H$_5$ | · | $\xrightarrow[99]{}$ | — | — | — | — | · |
|  | " | " | S | S | " | " | · | $\xrightarrow[98]{}$ | — | — | — | — | · |
| 9 | n-C$_5$H$_{11}$ | " | R | S | " | n-C$_{11}$H$_{23}$ | · | $\xrightarrow[122]{}$ | — | — | — | — | · |
|  | " | " | S | S | " | " | · | $\xrightarrow[105]{}$ | — | — | — | — | · |
| 10 | n-C$_9$H$_{19}$ | " | R | S | " | CH$_3$ | · | $\xrightarrow[102]{}$ | — | — | — | — | · |
|  | " | " | S | S | " | " | · | $\xrightarrow[85]{}$ | — | — | — | — | · |

TABLE 2-continued

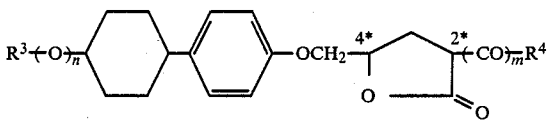

| Ex. No. | R³ | n | 2* | 4* | m | R⁴ | C | Sm1 | SmC* | SmA | N* | I |
|---|---|---|---|---|---|---|---|---|---|---|---|---|
| 11 | n-C₉H₁₉ | " | R | S | " | n-C₅H₁₁ | · $\xrightarrow{117}$ | — | — | — | — | · |
|  | " | " | S | S | " | " | · $\xrightarrow{98}$ | — | — | — | — | · |

EXAMPLE 12

The R isomer of glycidyl ether prepared in Preparation 5 (380 mg), dimethyl malonate (274 mg), potassium t-butoxide (163 mg) and t-butyl alcohol (2ml) are mixed, and the mixture is refluxed with stirring for 2 hours. The reaction mixture is cooled to room temperature and thereto is added dropwise 4N hydrochloric acid until pH 1. The mixture is extracted three times with chloroform, and the extract is washed with a saturated saline solution, dried over anhydrous magnesium sulfate and distilled under reduced pressure to remove the solvent. The residue is purified by silica gel chromatography to give 4R isomer of methoxycarbonyl-γ-lactone derivative (220 mg) of the following formula:

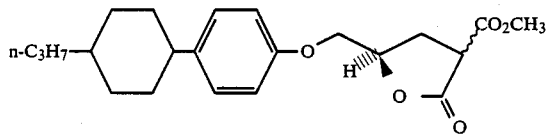

IR (KBr): 1781, 1744 cm$^{-1}$

The above γ-lactone derivative (200 mg), magnesium chloride (232 mg), dimethylacetamide (1.5 ml) and water (0.5 ml) are mixed and the mixture is refluxed with stirring for 10 hours. The reaction mixture is cooled to room temperature and extracted twice with chloroform. The extract is washed with a saturated saline solution, dried over anhydrous magnesium sulfate and distilled under reduced pressure to remove the solvent. The residue is purified by silica gel chromatography to give 4R isomer of γ-lactone derivative (145 mg) of the following formula:

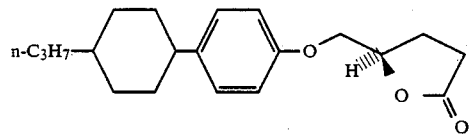

Phase transfer temperature:

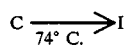

$[\alpha]_D^{30} = -18.64°$ (c=1.27, CH₂Cl₂)
NMR (CDCl₃) δ: 0.65–3.45 (21H, m), 3.90–4.30 (2H, m), 4.55–5.00 (1H, m), 6.77 (2H, d, J=9.0 Hz) 7.11 (2H, d, J=9.0 Hz)
IR (KBr): 1778 cm$^{-1}$

EXAMPLE 13

The S isomer of glycidyl ether prepared in Preparation 3 (370 mg), diethyl n-propylmalonte (442 mg), potassium t-butoxide (134 mg) and t-butyl alcohol (3 ml) are mixed, and the mixture is refluxed with stirring for 10 hours. The reaction mixture is cooled to room temperature and thereto is added dropwise 4N hydrochloric acid until pH 1. The mixture is washed with water and methanol to give white crystals. The product is separated and silica gel chromatography to give γ-lactone derivatives, (2S, 4S) isomer (240 mg) and (2R, 4S) isomer (140 mg) of the following formulae:

(2S, 4S) isomer:

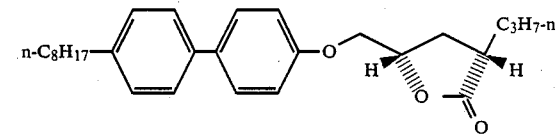

Phase transfer temperature:

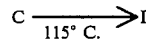

$[\alpha]_D^{26} = +32.67°$ (c=1.081, CH₂Cl₂)
NMR (CDCl₃) δ: 0.70–3.00 (27H, m), 4.00–4.25 (2H, m). 4.40–4.85 (1H, m), 6.60–7.60 (8H, m)
IR (KBr): 1762 cm$^{-1}$ (2R, 4S) isomer:

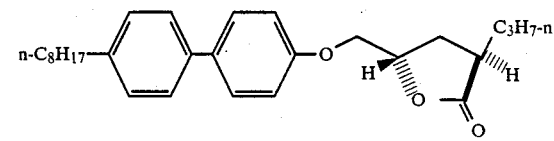

Phase transfer temperature:

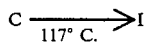

$[\alpha]_D^{26} = +22.50°$ (c=0.504, CH₂Cl₂)
NMR (CDCl₃) δ: 0.70–3.00 (27H, m), 4.00–4.25 (2H, m), 4.50–5.00 (1H, m), 6.60–7.60 (8H, m)
IR (KBr): 1762 cm$^{-1}$

EXAMPLE 14

The S isomer of glycidyl ether prepared in Preparation 4 (260 mg), dimethyl n-octylmalonate (269 mg), potassium t-butoxide (90 mg) and t-butyl alcohol (2 ml)

are mixed, and the mixture is refluxed with stirring for 13 hours. After the reaction, the reaction mixture is treated in the same manner as described in Example 13 to give white crystals. The product is separated and purified by silica gel chromatography to give a γ-lactone derivative, (2S, 4S) isomer (43 mg) of the following formula:

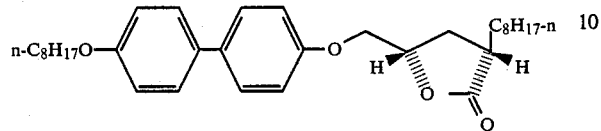

Phase transfer temperature:

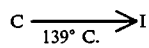

$[\alpha]_D^{30} = +28.59°$ (c=0.674, CH$_2$Cl$_2$)
NMR (CDCl$_3$) δ: 0.70–2.95 (37H, m), 3.80–4.20 (4H, m), 4.45–4.90 (1H, m), 6.90 (4H, d, J=9.0 Hz), 7.42 (4H, d, J=9.0 Hz)
IR (KBr): 1760 cm$^{-1}$

EXAMPLE 15

In the same manner as described in Example 13 except that the isomer of glycidyl ether prepared in Preparation 6 is used as the optically active glycidyl ether and dimethyl n-butylmalonate is used instead of dimethyl n-propylmalonate, there are prepared γ-lactone derivatives, (2R, 4R) isomer and (2S, 4R) isomer of the following formulae:

(2R, 4R) isomer:

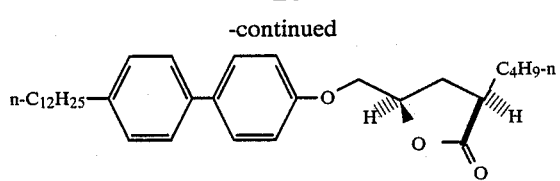

Phase transfer temperature:

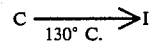

$[\alpha]_D^{34} = -28.56°$ (c=1.06, CH$_2$Cl$_2$)
NMR (CDCl$_3$)δ: 0.85–2.69 (37H, m), 4.15–4.18 (2H, m), 4.71–4.77 (1H, m), 6.95–7.53 (8H, m)
IR (KBr): 1764 cm$^{-1}$ (2S, 4R) isomer:

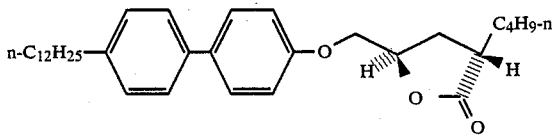

Phase transfer temperature:

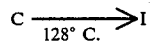

$[\alpha]_D^{34} = -22.98°$ (c=1.07, CH$_2$Cl$_2$)
NMR (CDCl$_3$) δ: 0.85–2.85 (37H, m), 4.08–4.21 (2H, m), 4.81–4.86 (1H, m), 6.93–7.52 (8H, m)
IR (KBr): 1760 cm$^{-1}$

EXAMPLES 16 to 22

In the same manner as described in Examples 13 to 14, there are prepared optically active γ-lactone derivatives as shown in Table 3, wherein R$^3$, R$^4$, n, m, and symbols 2* and 4* are of the following formula:

TABLE 3

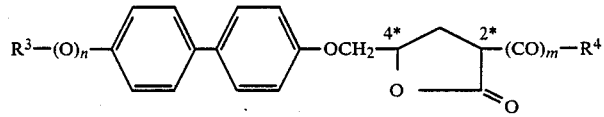

| Ex. No. | R$^3$ | n | 2* | 4* | m | R$^4$ | C | | Sm1 | SmC* | SmA | N* | I |
|---|---|---|---|---|---|---|---|---|---|---|---|---|---|
| 16 | n-C$_6$H$_{13}$ | 0 | R | S | 0 | CH$_3$ | · | $\xrightarrow{129}$ | — | — | — | — | · |
|  | " | " | S | S | " | " | · | $\xrightarrow{125}$ | — | — | — | — | · |
| 17 | n-C$_6$H$_{13}$ | " | R | S | " | n-C$_6$H$_{13}$ | · | $\xrightarrow{136}$ | — | — | — | — | · |
|  | " | " | S | S | " | " | · | $\xrightarrow{140}$ | — | — | — | — | · |
| 18 | n-C$_6$H$_{13}$ | " | R | S | " | n-C$_{10}$H$_{21}$ | · | $\xrightarrow{132}$ | — | — | — | — | · |
|  | " | " | S | S | " | " | · | $\xrightarrow{136}$ | — | — | — | — | · |
| 19 | n-C$_8$H$_{17}$ | " | R | S | " | CH$_3$ | · | $\xrightarrow{129}$ | — | — | — | — | · |
|  | " | " | S | S | " | " | · | $\xrightarrow{127}$ | — | — | — | — | · |
| 20 | n-C$_8$H$_{17}$ | 0 | R | S | 0 | n-C$_9$H$_{19}$ | · | $\xrightarrow{132}$ | — | — | — | — | · |
|  | " | " | S | S | " | " | · | $\xrightarrow{134}$ | — | — | — | — | · |

TABLE 3-continued

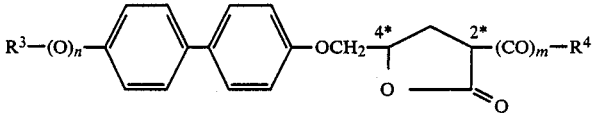

| Ex. No. | $R^3$ | n | 2* | 4* | m | $R^4$ | C | Sm1 | SmC* | SmA | N* | I |
|---|---|---|---|---|---|---|---|---|---|---|---|---|
| 21 | n-$C_8H_{17}$ | " | R | S | " | n-$C_{12}H_{25}$ | · $\xrightarrow{130}$ | — | — | — | — | · |
|  | " | " | S | S | " | " | · $\xrightarrow{133}$ | — | — | — | — | · |
| 22 | n-$C_8H_{17}$ | 1 | R | S | " | $CH_3$ | · $\xrightarrow{133}$ | — | — | — | — | · |
|  | " | " | S | S | " | " | · $\xrightarrow{119}$ | — | — | — | — | · |

EXAMPLE 23

In the same manner as described in Example 12 except that the S isomer of glycidyl ether prepared in Preparation 11 (365 mg), dimethyl malonate (232 mg) and potassium t-butoxide (138 mg) are used, there is prepared 4S isomer of 2-(methoxycarbonyl)-γ-lactone derivative (226 mg) of the following formula:

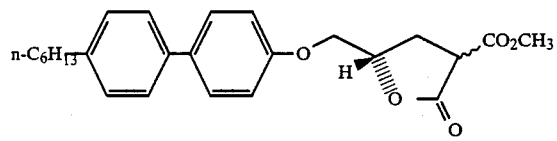

IR (KBr): 1740, 1768 cm$^{-1}$

The γ-lactone derivative of the above formula is hydrolyzed and decarboxylated in the same manner as described in Example 12, there is prepared 4S isomer of γ-lactone derivative (145 mg) of the following formula:

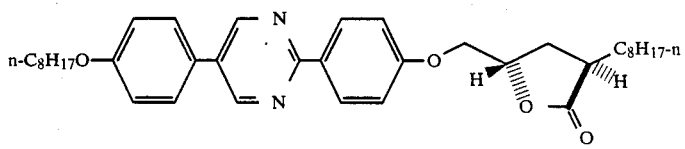

Phase transfer temperature: C $\xrightarrow{138° C.}$ I $[\alpha]_D^{30} = +19.16°$ (c=1.03, $CH_2Cl_2$)

NMR (CDCl$_3$) δ: 0.80–1.75 (11H, m), 2.15–2.85 (6H, m), 4.05–4.30 (2H, m), 4.75–4.95 (1H, m), 6.85–7.60 (8H, m)

IR (KBr): 1764 cm$^{-1}$

EXAMPLE 24

The S isomer of glycidyl ether prepared in Preparation 8 (518 mg), dimethyl n-octylmalonate (1170 mg) and potassium t-butoxide (269 mg) are dissolved in dimethylformamide (5 ml) and t-butyl alcohol (5 ml), and the mixture is heated with stirring at 90° C. for 5 hours. After the reaction, the reaction mixture is treated in the same manner as described in Example 13 to give γ-lactone derivatives (742 mg) of the following formulae. The product is a mixture of diastereomers and is purified by silica gel chromatography to give (2S, 4S) isomer and (2R, 4S) isomer.

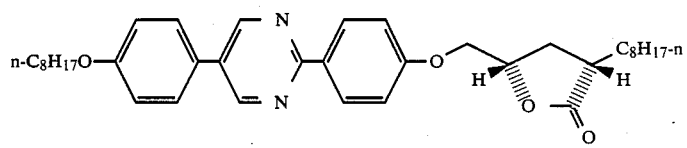

Phase transfer temperature: C $\underset{161° C.}{\overset{152° C.}{\rightleftarrows}}$ SmC* $\underset{186° C.}{\overset{185° C.}{\rightleftarrows}}$ I $[\alpha]_D^{28} = +19.45°$ (c=0.613, $CH_2Cl_2$)

NMR (CDCl$_3$) δ: 04–3.0 (35H, m), 3.7–4.3 (4H, m), 4.71 (1H, m), 7.00 (4H, d, J=9.0 Hz), 7.50 (2H, d, J=9.0 Hz), 8.39 (2H, d, J=9.0 Hz), 8.89 (2H, s)

IR (nujol): 1778 cm$^{-1}$

Phase transfer temperature: C $\underset{126° C.}{\overset{112° C.}{\rightleftarrows}}$ SmC* $\underset{199° C.}{\overset{198° C.}{\rightleftarrows}}$ I $[\alpha]_D^{28} = +7.09°$ (c=0.115, CH$_2$Cl$_2$)

NMR (CDCl$_3$) δ: 0.4–3.0 (35H, m), 3.7–4.3 (4H, m), 4.82 (1H, m), 7.00 (4H, d, J=9.0 Hz), 7.50 (2H, d, J=9.0 Hz), 8.39 (2H, d, J=9.0 Hz), 8.85 (2H, s)

IR (nujol): 1778 cm$^{-1}$

EXAMPLE 25

The S isomer of glycidyl ether prepared in Preparation 7 (1.0 g), dimethyl n-butylmalonate (1.056 g) and potassium t-butoxide (63 mg) are dissolved in dimethylformamide (10 ml) and t-butyl alcohol (10 ml), and the mixture is heated with stirring at 90° C. for 2 hours. After the reaction, the reaction mixture is treated in the same manner as described in Example 13 to give γ-lactone derivatives (626 mg). The product is a mixture of diastereomers and is purified by silica gel chromatography to give (2S, 4S) isomer and (2R, 4S) isomer.

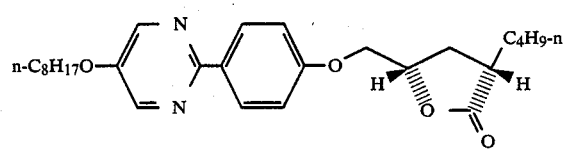

Phase transfer temperature: C $\xrightarrow{130° C.}$ I $[\alpha]_D^{27} = +41.04°$ (c=0.137, CH$_2$Cl$_2$)

NMR (CDCl$_3$) δ: 0.4–3.1 (27H, m), 3.9–4.3 (4H, m), 4.66 (1H, m), 6.92 (2H, d, J=9.0 Hz), 8.25 (2H, d, J=9.0 Hz), 8.35 (2H, s)

IR (nujol): 1776 cm$^{-1}$

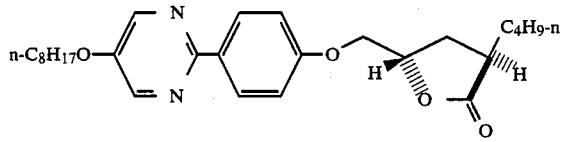

Phase transfer temperature: C $\xrightarrow{108° C.}$ I $[\alpha]_D^{27} = +25.02°$ (c=0.23, CH$_2$Cl$_2$)

NMR (CDCl$_3$) δ: 0.4–3.1 (27H, m), 3.9–4.3 (4H, m), 4.77 (1H, m), 6.92 (2H, d, J=9.0 Hz), 8.25 (2H, d, J=9.0 Hz), 8.35

IR (nujol): 1776 cm$^{-1}$

EXAMPLE 26

In the same manner as described in Example 25 except that the S isomer of glycidyl ether prepared in Preparation 10 is used as the optically active glycidyl ether and dimethyl n-dodecylmalonate is used instead of dimethyl n-butylmalonate, there are prepared γ-lactone derivatives, 2S, 4S) isomer and (2R, 4S) isomer.

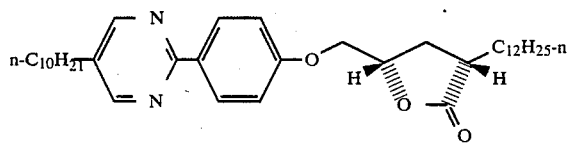

Phase transfer temperature: C $\xrightarrow{127° C.}$ I $[\alpha]_D^{31} = +26.01°$ (c=1.062, CH$_2$Cl$_2$)

NMR (CDCl$_3$ δ: 0.5–2.9 (49H, m), 4.19 (2H, mm), 4.82 (1H, m), 6.95 (2H, d, J=9.0 Hz), 8.32 (2H, d, J=9.0 Hz), 8.52 (2H, s)

IR (nujol): 1778 cm$^{-1}$

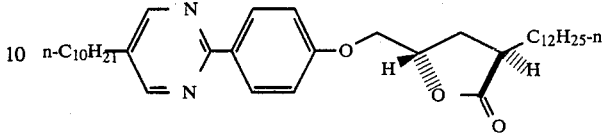

Phase transfer temperature: C $\xrightarrow{89° C.}$ I $[\alpha]_D^{31} = +17.12°$ (c=0.398, CH$_2$Cl$_2$)

NMR (CDCl$_3$) δ: 0.5–2.9 (49H, m), 4.19 (2H, m), 4.81 (1H, m), 6.95 (2H, d, J=9.0 Hz), 8.3 (2H, d, J=9.0 Hz), 8.52 (2H, s)

IR (nujol): 1778 cm$^{-1}$

EXAMPLE 27

The S isomer of glycidy ether prepared in Preparation 9 (320 mg), dimethyl n-hexylmalonate (406 mg) and potassium t-butoxide (116 mg) are dissolved in t-butyl alcohol (3.5 ml), and the mixture is refluxed with stirring for 6 hours. After the reaction, the reaction mixture is treated in the same manner as described in Example 13 to give a mixture of diastereomers of γ-lactone derivative (270 mg, (2S, 4S)/(2R, 4S)=9/1).

(2S, 4S) isomer:

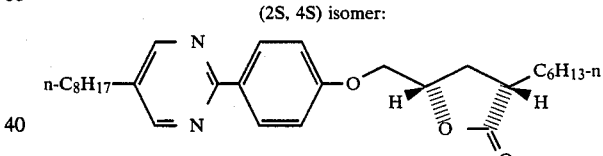

(2R, 4S) isomer:

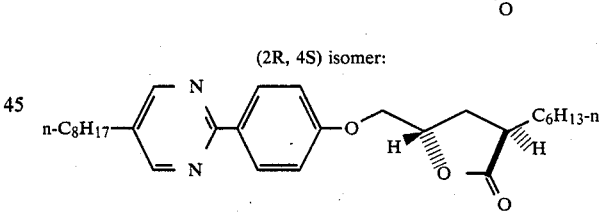

Physical properties of the mixture:

Phase transfer temperature: C $\xrightarrow{116° C.}$ I $[\alpha]_D^{25} = +37.93°$ (c=1.024, CH$_2$Cl$_2$)

NMR (CDCl$_3$) δ: 0.50–2.80 (33H, m), 4.10–4.25 (2H, m), 4.45–4.85 (1H, m), 6.95 (2H, d, J=9.0 Hz), 8.34 (2H, d, J=9.0 Hz), 8.52 (2H, s)

IR (nujol): 1778 cm$^{-1}$

EXAMPLES 28 to 33

In the same manner as described in Examples 24 to 27, there are prepared optically active γ-lactone derivatives as shown in Table 4, wherein R$^3$, R$^4$, n, e, m and the symbols 2* and 4* are of the following formula:

TABLE 4

R³—(O)ₙ—[phenyl]—[CH=N, N=CH]—[phenyl]—OCH₂—[4*]—[2*]—(CO)ₘ—R⁴ (γ-lactone)

| Ex. No. | R³ | n | e | 2* | 4* | m | R⁴ | C | SmI | SmC* | SmA | N* | I |
|---|---|---|---|---|---|---|---|---|---|---|---|---|---|
| 28 | n-C₈H₁₇ | 1 | 0 | R | S | 0 | CH₃ | • →115→ — | — | — | — | — | • |
|  | " | " | " | S | S | " | " | • →154→ — | — | — | — | — | • |
| 29 | n-C₈H₁₇ | " | " | R | S | " | n-C₇H₁₅ | • →102→ — | — | — | — | — | • |
|  | " | " | " | S | S | " | " | • →135→ — | — | — | — | — | • |
| 30 | n-C₈H₁₇ | " | " | R | S | " | n-C₁₀H₂₁ | • →100→ — | — | — | — | — | • |
|  | " | " | " | S | S | " | " | • →127→ — | — | — | — | — | • |
| 31 | n-C₈H₁₇ | " | 1 | R | S | " | n-C₅H₁₁ | • ⇄134/138 | • ⇄145/145 | • ⇄201/201 | — | • ⇄202/202 | • |
|  | " | " | " | S | S | " | " | • ⇄147/150 | • ⇄153/155 | • ⇄190/190 | — | — | • |
| 32 | n-C₈H₁₇ | 1 | 1 | R | S | 0 | n-C₁₁H₂₃ | • ⇄114/120 | • ⇄131/133 | • ⇄192/195 | — | — | • |
|  | " | " | " | S | S | " | " | • ⇄147/150 | • ⇄155/155 | • ⇄180/183 | — | — | • |
| 33 | n-C₁₀H₂₁ | 0 | 0 | R | S | " | n-C₉H₁₉ | • →100→ — | — | — | — | — | • |
|  | " | " | " | S | S | " | " | • →139→ — | — | — | — | — | • |

Figure 2:
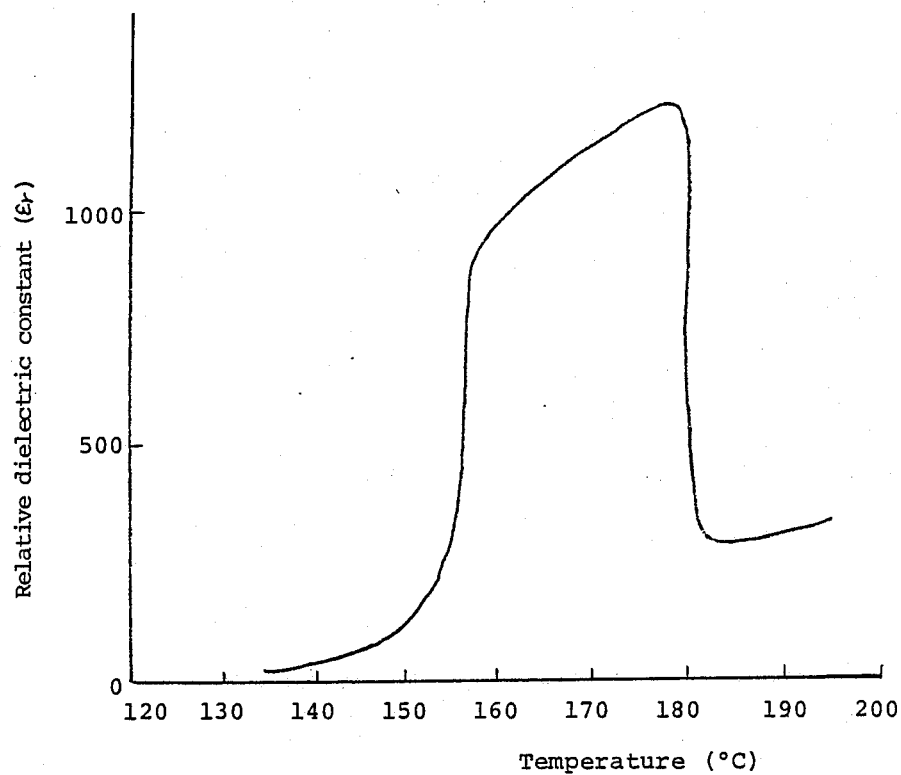
FIG. 2 shows a graph of the relation between the relative dielectric constant and temperature in the γ-lactone derivative (2S, 4S) prepared in Example 32.

The γ-lactone derivative (2S, 4S) prepared in Example 32 was sealed in a cell made of glass(thickness of spacer: 22 μm). The cell was charged with alternating current (70 Hz, 1V), and the relative dielectric constant was measured by bridge method. The results are shown in the accompanying FIG. 2. It is clear from the test results that the compound has ferroelectric property.

What is claimed is:

1. A liquid crystalline compound having an optically active γ-lactone ring of the formula:

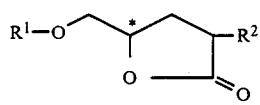

(A)

wherein R¹ is a group selected from the group consisting of

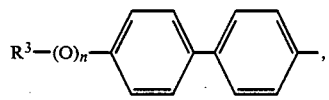

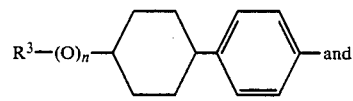

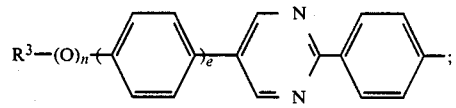

n and e are each independently 0 or 1; R³ is an alkyl group having 1 to 15 carbon atoms; R² is a group of the formula: —(CO)ₘ—R⁴; m is 0 or 1; R⁴ is hydrogen atom or an alkyl group having 1 to 15 carbon atoms; and the symbol * is an asymmetric carbon atom.

2. The compound according to claim 1, which is in the form of a racemic mixture.

3. The compound according to claim 1, wherein $R^1$ is a group of the formula:

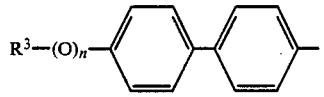

wherein n is 0 or 1 and $R^3$ is an alkyl group having 1 to 15 carbon atoms; and $R^2$ is a group of the formula: $-(CO)_m-R^4$ wherein m is 0 and $R^4$ is hydrogen atom or an alkyl group having 1 to 15 carbon atoms.

4. The compound according to claim 1, wherein $R^1$ is a group of the formula:

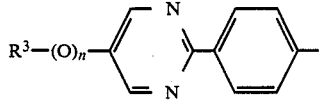

wherein n is 0 or 1 and $R^3$ is an alkyl group having 1 to 15 carbon atoms; and $R^2$ is a group of the formula: $-(CO)_m-R^4$ wherein m is 0 and $R^4$ is hydrogen atom or an alkyl group having 1 to 15 carbon atoms.

5. The compound according to claim 1, wherein $R^1$ is a group of the formula:

wherein n is 0 or 1 and $R^3$ is an alkyl group having 1 to 15 carbon atoms; and $R^2$ is a group of the formula: $-(CO)_m-R^4$ wherein m is 0 and $R^4$ is hydrogen atom or an alkyl group having 1 to 15 carbon atoms.

* * * * *